United States Patent
Filippi (12)

(10) Patent No.: US 6,333,014 B1
(45) Date of Patent: Dec. 25, 2001

(54) PROCESS FOR AMMONIA AND METHANOL CO-PRODUCTION

(75) Inventor: Ermanno Filippi, Castagnola (CH)

(73) Assignee: Methanol Casale S.A., Lugano-Besso (CH)

( * ) Notice: Subject to any disclaimer, the term of this patent is extended or adjusted under 35 U.S.C. 154(b) by 0 days.

(21) Appl. No.: 09/029,358

(22) PCT Filed: Aug. 23, 1996

(86) PCT No.: PCT/IB96/00830

§ 371 Date: Feb. 24, 1998

§ 102(e) Date: Feb. 24, 1998

(87) PCT Pub. No.: WO97/10194

PCT Pub. Date: Mar. 20, 1997

(30) Foreign Application Priority Data

Sep. 11, 1995 (CH) .................................................. 02572/95

(51) Int. Cl.$^7$ .............................. C01C 1/04; B01D 50/00; C07C 27/06
(52) U.S. Cl. ........................... 423/359; 422/170; 422/171; 518/704
(58) Field of Search ..................... 422/171, 170; 423/359; 518/704

(56) References Cited

U.S. PATENT DOCUMENTS

| | | |
|---|---|---|
| 3,598,527 | 8/1971 | Quartulli et al. . |
| 4,315,900 | 2/1982 | Nozawa et al. . |
| 4,367,206 * | 1/1983 | Pinto .................................... 423/359 |
| 4,681,745 * | 7/1987 | Pinto .................................... 423/359 |
| 5,167,933 * | 12/1992 | Norsk ................................... 423/359 |

FOREIGN PATENT DOCUMENTS

| | | | |
|---|---|---|---|
| 3336649 | 4/1985 | (DE) . | |
| 0011404 | 5/1980 | (EP) . | |
| 154314 * | 12/1980 | (JP) .................................... | 423/359 |

OTHER PUBLICATIONS

"Steam hydrocarbon reforming seen as integrated processing hub", O.J. Quartulli, Oil and Gas Journal, vol. 70, No. 2, Jan. 10, 1972, Tulsa, OK, USA, pp. 53–58.

* cited by examiner

Primary Examiner—Wayne Langel
(74) Attorney, Agent, or Firm—Sughrue Mion, PLLC

(57) ABSTRACT

A process for ammonia and methanol co-production in a plant comprising a secondary reformer section, a high-temperature CO conversion section and a low-temperature CO conversion section, arranged in series, and an ammonia synthesis section, is distinguished by the fact that the unreacted gas flow coming from a methanol synthesis section, before being fed to the low-temperature CO conversion section, is advantageously saturated with a liquid flow comprising $H_2O$ appropriately heated by indirect heat exchange with a gaseous flow coming from the secondary reformer section.

8 Claims, 1 Drawing Sheet

PROCESS FOR AMMONIA AND METHANOL CO-PRODUCTION

FIELD OF APPLICATION

The present invention relates to a process for the ammonia and methanol co-production in a plant comprising a secondary reformer section, a high-temperature CO conversion section and a low-temperature CO conversion section, arranged in series, and an ammonia synthesis section, the process comprising the steps of:

taking a gaseous flow comprising CO, $CO_2$, $H_2$ and $H_2O$ coming from said secondary reformer section;

feeding the gaseous flow to a cooling and $H_2O$ separation section;

cooling said gaseous flow and separating the $H_2O$ contained therein in said cooling and $H_2O$ separation section;

feeding a substantially $H_2O$-free gaseous flow coming from said cooling and $H_2O$ separation section to a methanol synthesis section;

reacting said substantially $H_2O$-free gaseous flow in said synthesis section for methanol production;

feeding a gaseous flow comprising CO, $CO_2$, $H_2$ and $CH_3OH$ coming from said methanol synthesis section to a methanol separation section;

separating a fluid flow comprising methanol from a substantially methanol-free gaseous flow and comprising CO, $CO_2$, and $H_2$ in said methanol separation section, and feeding said substantially methanol-free gaseous flow coming from said methanol separation section to said low-temperature CO conversion section.

The present invention also relates to a plant for ammonia and methanol co-production for carrying out the above mentioned process, and to a modernization method for an ammonia synthesis plant.

As known, there is an ever growing requirement in the field of ammonia and methanol co-production to provide easily implemented synthesis processes, which allow achievement of the desired production capacity at low operating and investment costs and with low energy consumption.

PRIOR ART

For the purpose of meeting the above mentioned requirement, there have recently been proposed in the field synthesis processes for ammonia and methanol co-production, wherein a flow of gas rich in CO, $CO_2$ and $H_2$ coming from the secondary reformer section of an ammonia synthesis plant, is diverted to a section for condensation and separation of the water contained therein and then conveyed into a synthesis section for methanol production. The unreacted gas is subsequently reintroduced downstream of the high-temperature CO conversion section of the ammonia plant.

Although advantageous in some ways, the above described process exhibits a series of drawbacks, the first of which is the fact that the unreacted gaseous flow coming from the methanol synthesis section before being returned into the ammonia synthesis process is mixed with a steam flow at high or medium pressure to bring the temperature and the $H_2O$ concentration to values such as to aid the subsequent CO conversion.

It follows that, due to high steam consumption, operating costs and energy consumption resulting from the ammonia and methanol co-production process according to the prior art are such as to considerably frustrate the advantages deriving from utilization of the gas present in the ammonia plant for methanol production.

In addition, in the process just described, the methanol is produced in a reaction section comprising a synthesis loop, at a pressure generally comprised between 50 bar and 100 bar, which is substantially higher than the pressure present in the secondary reformer section of the ammonia plant.

For this reason the plant for carrying out the process according to the prior art requires special equipment for recycling of the unreacted gas to the synthesis reactor and for compression of the gas flow coming from the secondary reformer section, thus involving high structural complexity as well as high investment costs.

SUMMARY OF THE INVENTION

The problem underlying the present invention is to provide a process for ammonia and methanol co-production which would be simple to apply and permit achieving the desired production capacity at low operating and investment costs in addition to low energy consumption.

The above mentioned problem is solved according to the present invention by a process for ammonia and methanol co-production of the above mentioned type, which is characterized in that it comprises the step of feeding to the substantially methanol-free gaseous flow coming from the methanol separation section a liquid flow comprising $H_2O$ appropriately heated by indirect heat exchange with the gaseous flow coming from the secondary reformer section.

Advantageously, it is possible to achieve effective saturation with $H_2O$ and temperature regulation of the substantially methanol-free gaseous flow to be conveyed to the low-temperature CO conversion section, by utilizing indirectly the heat of the gaseous flow coming from the secondary reformer.

There is thus avoided utilization of energy sources external to the ammonia and methanol co-production process as for example, with reference to the prior art, introduction of water in steam form, and therefore energy consumption is considerably reduced.

Preferably, the temperature of the liquid flow comprising $H_2O$ fed to the substantially methanol-free gaseous flow is between 100° C. and 300° C., so that the temperature of the gaseous flow returned to the ammonia synthesis process is such as to aid the conversion reaction in the low-temperature CO conversion section.

In addition, in accordance with a particularly advantageous embodiment of the process according to the present invention the liquid flow containing $H_2O$ comes at least partly from the cooling and $H_2O$ separation section.

In this manner, the process according to the present invention allows recovery and utilization of the water obtained by condensation in the cooling and $H_2O$ separation section upstream of the methanol synthesis section, by recirculating it to the unreacted gaseous flow before it is returned to the ammonia synthesis process.

Consequently, the concentration of $H_2O$ in the gaseous flow conveyed to the low-temperature CO conversion section can be advantageously controlled by limiting or even eliminating the necessity of adding outside water to the ammonia and methanol co-production process, while achieving a simplification of the plant and reducing operating and investment costs and energy consumption.

Advantageously, the substantially $H_2O$-free gaseous flow is reacted in a synthesis section for methanol production of the 'once-through' type. This allows simplification of the synthesis section equipment, and hence considerable reduction of investment costs as compared with a plant provided with a methanol reaction section including a synthesis loop of the type described with reference to the prior art.

In the following description and the annexed claims, the term: synthesis section of the 'once-through' type, is understood to mean a reaction section in which the unreacted effluents are not recycled to the synthesis reactor.

For carrying out the above mentioned process, the present invention advantageously makes available a plant for ammonia and methanol co-production comprising:

- a secondary reformer section, a high-pressure CO conversion section and a low-temperature CO conversion section, arranged in series;
- an ammonia synthesis section in fluid communication with the low-temperature CO conversion section;
- a cooling and separation section for the $H_2O$ contained in a gaseous flow coming from said secondary reformer section and also comprising CO, $CO_2$ and $H_2$;
- a synthesis section for methanol production fed by a substantially $H_2O$-free gaseous flow coming from said cooling and $H_2O$ separation section;
- a methanol separation section fed by a gaseous flow coming from said methanol synthesis section for separation of a fluid flow comprising methanol from a substantially methanol-free gaseous flow and comprising CO, $CO_2$ and $H_2$;
- an $H_2O$ saturation section for said substantially methanol-free gaseous flow in fluid communication with the low-temperature CO conversion section;

which is characterized in that it comprises a heating section for a liquid flow comprising $H_2O$ for indirect heat exchange with said gaseous flow coming from said secondary reformer section in fluid communication with said saturation section.

In accordance with another aspect of the present invention there is also made available a modernization method for an ammonia synthesis plant of the type comprising a secondary reformer section, a high-temperature CO conversion section and a low-temperature CO conversion section, arranged in series, and an ammonia synthesis section, said method comprising the steps of:

- providing a cooling and separation section for the $H_2O$ contained in the gaseous flow coming from said secondary reformer section and also comprising CO, $CO_2$ and $H_2$;
- providing a synthesis section for methanol production fed by a substantially $H_2O$-free gaseous flow coming from said cooling and $H_2O$ separation section;
- providing a methanol separation section fed by a gaseous flow coming from said methanol synthesis section for separation of a fluid flow comprising methanol from a substantially methanol-free gaseous flow comprising CO, $CO_2$ and $H_2$;
- providing a $H_2O$ saturation section for said substantially methanol-free gaseous flow;
- providing a heating section for a liquid flow comprising $H_2O$ for indirect heat exchange with said gaseous flow coming from said secondary reformer section;
- providing connection means between said heating section and said saturation section to feed a liquid flow comprising appropriately heated $H_2O$ to said saturation section; and
- providing connection means between said saturation section and said low-temperature CO conversion section to feed to said CO conversion section a gaseous flow comprising CO, $CO_2$, $H_2$ and $H_2O$.

Thanks to this modernization method for an existing ammonia synthesis plant it is possible to obtain a process for the co-production of ammonia and methanol simple to implement and capable of achieving the desired production capacity at low operating and investment costs and with low energy consumption.

The characteristics and advantages of the present invention are set forth in the description of an embodiment thereof given below by way of non-limiting example with reference to the annexed figure.

DETAILED DESCRIPTION OF A PREFERRED EMBODIMENT

Figure 1:
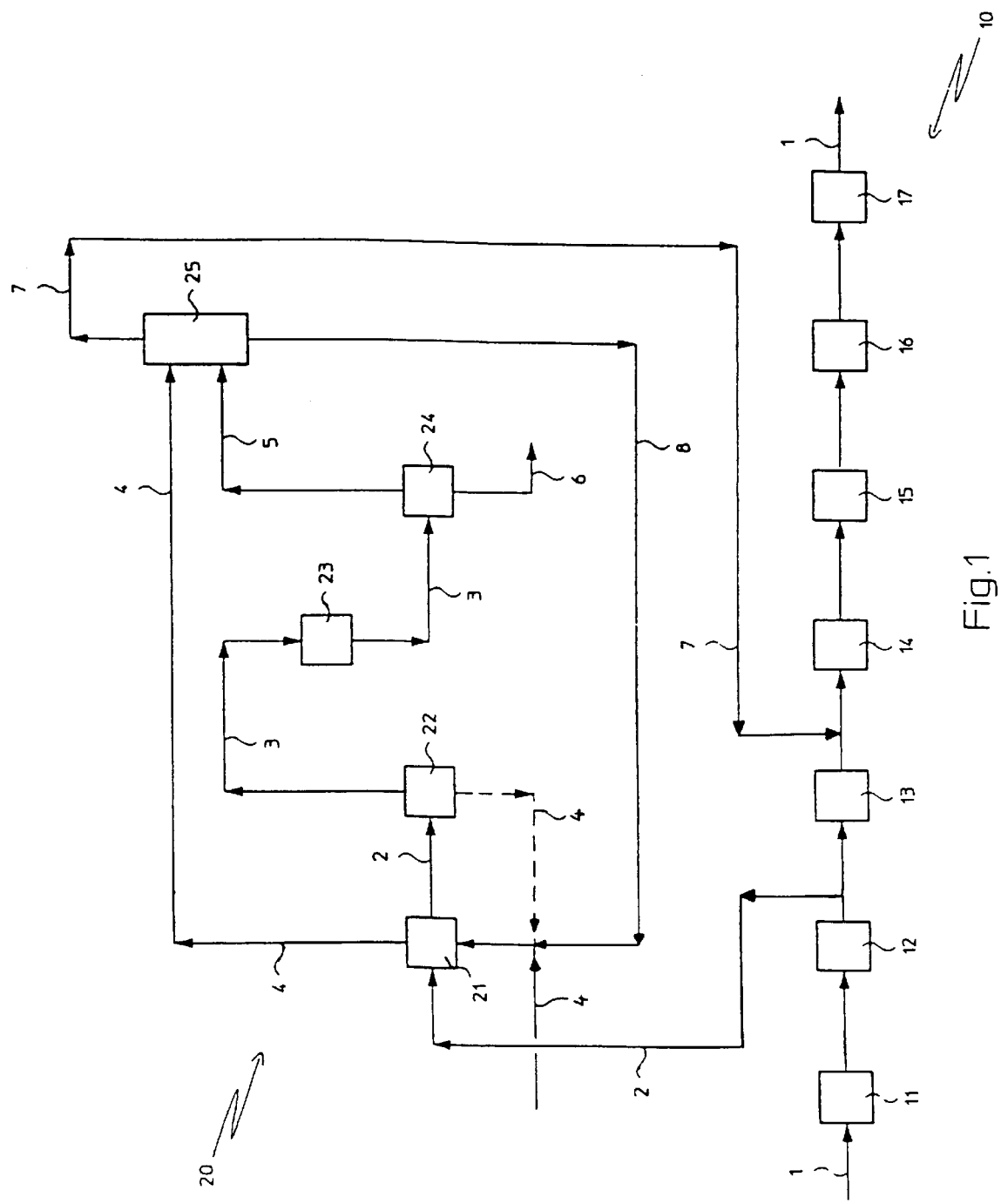
FIG. 1 shows a block diagram of the ammonia and methanol co-production process according to the present invention.

FIG. 1 shows a block diagram illustrating the steps of the ammonia and methanol co-production process, according to the present invention.

Reference number 10 indicates generally a portion of the block diagram illustrating the steps of the ammonia production process.

In this portion 10, blocks 11–17 indicate respectively a primary reformer section, a secondary reformer section, a high-temperature CO conversion section, a low-temperature CO conversion section, a $CO_2$ separation section, a methanation section and an ammonia synthesis section.

Blocks 11–17 are traversed by a flow line 1 representing a gaseous flow having a composition varying with the passage through the different reaction sections.

For example, at the input to the primary reformer section indicated by block 11, the gas flow 1 comprises substantially methane or natural gas while at the output from the ammonia synthesis section, represented by block 17, it comprises mainly ammonia.

The operating conditions of the ammonia production process, just as the type of reactions taking place during the passage of the gaseous flow through the various sections, are the conventional ones of a high pressure and temperature ammonia plant, known to those skilled in the art and therefore not further described.

Reference number 20 indicates generally a portion of the block diagram illustrating the steps of the methanol production process.

In this portion 20, blocks 21–25 indicate respectively a cooling section, an $H_2O$ separation section, a methanol synthesis section, a methanol separation section and a section for saturation with $H_2O$ of the unreacted substantially methanol-free gaseous flow.

Flow line 2 represents a gaseous flow coming from the flow line 1 leaving the secondary reformer section indicated by block 12, and comprising CO, $CO_2$, $H_2$ and $H_2O$.

Flow line 2 traverses the cooling section represented by block 21, where the larger part of the steam contained in the gaseous flow condenses, and is fed to the $H_2O$ separation section indicated by block 22.

Coming from block 22 is represented flow line 3 of a gaseous flow comprising CO, $CO_2$ and $H_2$.

Flow line 3 traverses the methanol synthesis section represented by block 23, where a part of the reagents contained in the gaseous flow is reacted to obtain methanol, and is fed to the separation section indicated by block 24, which separates the unreacted gas flow comprising CO, $CO_2$ and $H_2$ from the methanol.

Flow line 6 indicates the methanol flow thus obtained, while flow line 5 represents the unreacted substantially methanol-free gaseous flow which is fed to the saturation section represented by block 25.

Advantageously, at the inlet to block 25 is also fed flow line 4 of a liquid flow comprising $H_2O$ which has been previously heated in block 21 by indirect heat exchange with the gaseous flow coming from the secondary reformer section.

As shown in FIG. 1, coming from block 25, representing the saturation section of the unreacted substantially methanol-free gaseous flow, there departs a flow line 7 of a gaseous flow containing CO, $CO_2$, $H_2$ and $H_2O$ which is fed back to flow line 1 of the ammonia synthesis process upstream of the low-temperature CO conversion section indicated by block 14.

From block 25 also departs a flow line 8 of a liquid flow comprising $H_2O$ which is recirculated to flow line 4 upstream of block 21.

According to the process of the present invention a gaseous flow comprising CO, $CO_2$, $H_2$ and $H_2O$ is taken from the secondary reformer section (block 12) and fed to a cooling (block 21) and $H_2O$ separation (block 22) section. Here the gaseous flow is cooled and the $H_2O$ contained therein separated. A substantially $H_2O$-free gaseous flow coming from the cooling and $H_2O$ separation section is then fed to a methanol synthesis section (block 23) where it reacts to be converted into methanol. The gaseous flow coming from the methanol synthesis section is then fed to a methanol separation section (block 24) for separation of a fluid flow comprising methanol from a substantially methanol-free gaseous flow comprising CO, $CO_2$ and $H_2$, which is in turn fed to the low-pressure CO conversion section (block 14).

Advantageously, in accordance with another step of the present process, a liquid flow comprising $H_2O$ appropriately heated by indirect heat exchange with the gaseous flow coming from the secondary reformer section is fed to the substantially methanol-free gaseous flow coming from the methanol separation section.

By operating in this manner, at least part of the heat of the gaseous flow coming from the secondary reformer is advantageously recovered to aid saturation in $H_2O$ and heating of the gaseous flow to be conveyed to the low-temperature CO conversion section.

In the example of FIG. 1, the heating of the liquid flow comprising $H_2O$ takes place in the cooling section indicated by block 21.

Preferably, the liquid flow comprising $H_2O$ fed to the saturation section (block 25) is heated previously, according to the present, invention to a temperature between 150° C. and 280° C., so as to bring the temperature of the substantially methanol-free gaseous flow to be fed back to the ammonia synthesis process back to values such as to aid the successive conversion of the CO. These values are generally comprised between 180° C. and 250° C.

In a particular and advantageous embodiment of the process according to the present invention, but not shown, the liquid flow comprising $H_2O$ is appropriately compressed before being heated, and is subjected after heating to an expansion step to achieve flash evaporation of part of the $H_2O$ contained in the liquid flow to be fed to the substantially methanol-free gaseous flow.

In this manner, the liquid flow being fed to the saturation section (block 25) comprises advantageously steam at high thermal level, which significantly facilitates saturation with $H_2O$ and heating of the gaseous flow coming from the methanol separation section (block 24).

Advantageously, the liquid flow comprising $H_2O$ coming from block 22 is compressed to a pressure between 20 bar and 100 bar, and preferable 60 bar.

In an alternative and particularly advantageous embodiment of the process according to the present invention, the liquid flow comprising $H_2O$ comes at least partly from the cooling and $H_2O$ separation section (blocks 21, 22).

In FIG. 1, this alternative embodiment is represented by the broken flow line 4'.

In this manner it is possible to use the $H_2O$ contained in the gaseous flow coming from the secondary reformer section, appropriately condensed and separated upstream of the methanol synthesis section, for saturation of the substantially methanol free unreacted gas flow to be fed back into the ammonia production process.

The cooling and $H_2O$ separation section and the saturation section have respectively the functions of eliminating at least part of the $H_2O$ contained in the gaseous reagents before the synthesis reaction takes place, to prevent the $H_2O$ (a reaction product) from acting as inhibitor of the conversion reaction, and of enriching with $H_2O$ the gaseous flow to be fed back into the ammonia synthesis process to aid the CO conversion reaction.

Thanks to the present invention, it is now possible to perform a saturation of the gaseous flow to be conveyed to the CO conversion section by directly utilizing the $H_2O$ previously obtained in the cooling and $H_2O$ separation section.

In an alternative embodiment of the process according to the present invention, the liquid flow comprising $H_2O$ fed to the substantially methanol-free gaseous flow comes entirely from the cooling and $H_2O$ separation section, thus eliminating the need for using a saturation flow fed from the outside.

According to the present invention, the substantially $H_2O$-free gaseous flow coming from the separation section indicated by block 22 is reacted in a synthesis section for methanol production (block 23) comprising advantageously a reactor of the 'once-through' type.

In comparison with the ammonia and methanol co-production processes of the prior art, which utilize a methanol synthesis section of the type comprising a synthesis loop, the present invention permits elimination of all that part of the equipment associated with recycling to the synthesis reactor of at least part of the unreacted gaseous reagents, thus considerably reducing investment costs and energy consumption.

In an alternative embodiment of the present invention, not shown, it is also possible to provide a methanol synthesis section (block 23) comprising a plurality of 'once-through' reactors arranged in series to achieve a high degree of conversion of the gaseous reagents. This embodiment is particularly suited in those cases where there is the requirement to produce high quantities of methanol.

The methanol separation section, represented in FIG. 1 by block 24, for separation of the unreacted gas flow from the flow of methanol produced, is generally made up of a separation vessel in which the gas is cooled to approximately room temperature with resulting condensation of the methanol contained therein.

Advantageously, the pressure conditions used in the methanol synthesis process are approximately the same as those for the ammonia synthesis process.

The pressure in the methanol production part of the process according to the present invention is advantageously between 20 bar and 50 bar.

In fact, it was found that it is possible to obtain in the methanol synthesis section (block 23) a satisfactory conversion yield even when operating with pressures similar to those of the ammonia production part of the process.

In this manner the plant for carrying out the process can be further simplified, with resulting reduction of operating and investment costs and energy consumption, since it is no longer necessary to use compressors as employed in the methanol and ammonia co-production process in accordance with the prior art.

Lastly, according to the process of the present invention the gaseous flow coming from the secondary reformer section is cooled in the cooling section (block 21) to a temperature preferably below 50° C.

It was found that below this temperature there is obtained a nearly complete condensation of the steam contained in the gaseous flow coming from the secondary reformer section (block 12), to the benefit of the subsequent methanol synthesis steps (block 23) and, in case of at least partial recovery of the condensed water, of saturation with $H_2O$ (block 25) of the substantially methanol-free gaseous flow.

Thanks to the present invention there can be achieved an ammonia and methanol co-production process easy to implement, with low operating and investment costs and low energy consumption.

With reference to FIG. 1, the plant for ammonia and methanol co-production comprises the sections indicated by blocks 11–17 and 21–25.

Advantageously, the plant according to the present invention also provides a heating section for a liquid flow comprising $H_2O$ by indirect heat exchange with the gaseous flow coming from the secondary reformer section, in fluid communication with the saturation section.

In the example of FIG. 1, the section indicated by the block 21 also fulfils the function of heating the liquid flow comprising $H_2O$ before feeding it to the substantially methanol-free gaseous flow.

The cooling or heating section (block 21) can include one or more heat exchangers arranged in series and upstream of the $H_2O$ separation section (block 22), for removal by indirect heat exchange with a flow of cooling liquid including $H_2O$ of at least part of the heat present in the gaseous flow coming from the secondary reformer section (block 12) of the process for ammonia synthesis, so as to achieve condensation of the steam contained therein and simultaneously heating of the liquid flow comprising $H_2O$.

In an alternative embodiment, the plant according to the present invention also comprises suitable connection means (flow line 4') to bring about fluid communication between the $H_2O$ separation section and the heating section, so as to permit utilization of at least part of the $H_2O$ contained in the gaseous flow coming from the secondary reformer section (block 12) for saturation of the unreacted gas flow to be returned into the low-temperature CO conversion section (block 14).

The synthesis section 23 for methanol production is advantageously of the 'once-through' type.

With reference to the modernization method for an existing ammonia synthesis plant according to the present invention it is important to note that at least part of the gaseous flow coming from the secondary reformer and rich in CO, $CO_2$ and $H_2$, can be advantageously utilized for production of a product of commercial value such as methanol, while at the same time lightening the CO conversion and $CO_2$ separation sections of the ammonia plant.

In accordance with the different steps of the present modernization method for an ammonia synthesis plant, there are provided a cooling (block 21) and separation (block 22) section for the $H_2O$ contained in a gaseous flow coming from the secondary reformer section (block 12) of the ammonia plant, and a following synthesis section for methanol production (block 23) fed by a substantially $H_2O$-free gaseous flow coming from the cooling and $H_2O$ separation section. A methanol separation section (block 24) fed by a gaseous flow coming from the methanol synthesis section is provided for separation of a fluid flow comprising methanol from a substantially methanol-free gaseous flow comprising CO, $CO_2$ and $H_2$, which is saturated with $H_2O$ in a saturation section (block 25) appropriately provided.

Advantageously, there are also provided a heating section (block 21) for a liquid flow comprising $H_2O$ for indirect heat exchange with the gaseous flow coming from the secondary reformer section (block 12) and connection means between the heating section and the saturation section (flow line 4).

Lastly, between the saturation section and the low-temperature CO conversion section (block 14) are arranged connection means (flow line 7) to feed to the CO conversion section a gaseous flow comprising CO, $CO_2$, $H_2$ and $H_2O$.

In a particularly advantageous alternative embodiment, the modernization method according to the present invention also comprises the step of arranging appropriate connection means between the cooling and $H_2O$ separation section and the heating section (flow line 4'), to feed to the latter a liquid flow comprising $H_2O$.

From the foregoing the numerous advantages achieved by the present invention are clear. In particular there is provided a process for ammonia and methanol co-production easy to implement and capable of achieving the desired capacity at low operating and investment costs and low energy consumption.

What is claimed is:

1. Process for the ammonia and methanol co-production in a plant comprising a secondary reformer section, a high-temperature CO conversion section and a low-temperature CO conversion section, arranged in series, an ammonia synthesis section, a methanol synthesis section and a methanol separation section, said process comprising the following steps:

taking a portion of a gaseous flow comprising CO, $CO_2$, $H_2$ and $H_2O$ coming from said secondary reformer section;

feeding said portion of gaseous flow to a cooling and $H_2O$ separation section;

feeding a remaining portion of said gaseous flow comprising CO, $CO_2$, $H_2$ and $H_2O$ coming from said secondary reforming section to said high-temperature CO conversion section;

feeding a gaseous flow comprising CO, $CO_2$, $H_2$ and $H_2O$ coming from said high temperature CO conversion section to said low-temperature CO conversion section;

feeding a substantially $H_2O$-free gaseous flow coming from said cooling and $H_2O$ separation section to said methanol synthesis section;

reacting said substantially $H_2O$-free gaseous flow in said synthesis section for methanol production;

feeding a gaseous flow comprising CO, $CO_2$, $H_2$ and $CH_3OH$ coming from said methanol synthesis section to said methanol separation section;

separating a fluid flow comprising methanol from a substantially methanol-free gaseous flow comprising CO, $CO_2$ and $H_2$ in said methanol separation section;

feeding said substantially methanol-free gaseous flow coming from said methanol separation section to said low-temperature CO conversion section;

feeding a gaseous flow coming from said low-temperature CO conversion section to said ammonia synthesis section for ammonia production; and feeding to said substantially methanol-free gaseous flow coming from said methanol separation section a liquid flow comprising $H_2O$ heated by indirect heat exchange with said portion of gaseous flow coming from said secondary reformer section.

2. Process according to claim 1, wherein the temperature of the liquid flow comprising $H_2O$ fed to said substantially methanol-free gaseous flow is between 100° C. and 300° C.

3. Process according to claim 1, further comprising the steps of compressing said liquid flow comprising $H_2O$ before said heating by indirect heat exchange with the gaseous flow coming from said secondary reformer section, and expanding said liquid flow comprising $H_2O$ before said feeding to the substantially methanol-free gaseous flow to achieve flash evaporation of part of the $H_2O$ contained therein.

4. Process according to claim 3, wherein the pressure of the liquid flow comprising $H_2O$ after said compression step is between 20 bar and 100 bar.

5. Process according to claim 1, wherein said liquid flow comprising $H_2O$ comes at least partly from said cooling and $H_2O$ separation section.

6. Process according to claim 1, wherein the pressure in said synthesis section for methanol production is between 20 bar and 50 bar.

7. Process according to claim 1, wherein said gaseous flow coming from said secondary reformer section is cooled in said cooling and $H_2O$ separation section to a temperature below 50° C.

8. Plant for ammonia and methanol co-production comprising:

a secondary reformer section (12), a high-temperature CO conversion section (13) and a low-temperature CO conversion section (14), connected in series;

an ammonia synthesis section (17) in fluid communication with said low-temperature CO conversion section (14);

a cooling and separation section (21,22) connected to said secondary reforming section (12) for cooling and separating the $H_2O$ contained in a portion of a gaseous flow coming from said secondary reformer section (12) and also comprising CO, $CO_2$ and $H_2$;

a synthesis section for methanol production (23) fed by a substantially $H_2O$-free gaseous flow coming from said cooling and $H_2O$ separation section (21,22);

a methanol separation section (24) fed by a gaseous flow coming from said methanol synthesis section (23) for separation of a fluid flow comprising methanol from a substantially methanol-free gaseous flow comprising CO, $CO_2$ and $H_2$;

an $H_2O$ saturation section (25) for said substantially methanol-free gaseous flow in fluid communication with said low-temperature CO conversion section (14);

connection means between said saturation section (25) and said low temperature CO conversion section (14); and a heating section (21) for a liquid flow comprising $H_2O$ by indirect heat exchange with said portion of gaseous flow coming from said secondary reformer section (12), in fluid communication with said saturation section (25).

\* \* \* \* \*